United States Patent [19]

Celmer et al.

[11] 4,038,383

[45] July 26, 1977

[54] MIXTURE OF ANTIBIOTICS PRODUCED BY A SPECIES OF ACTINOPLANES

[75] Inventors: Walter D. Celmer, New London; Walter P. Cullen, East Lyme; Charles E. Moppet, Groton; John B. Routien, Lyme, all of Conn.; Riichiro Shibakawa, Handa; Junsuke Tone, Chita, both of Japan

[73] Assignee: Pfizer Inc., New York, N.Y.

[21] Appl. No.: 604,260

[22] Filed: Aug. 13, 1975

Related U.S. Application Data

[63] Continuation-in-part of Ser. No. 541,800, Jan. 17, 1975, abandoned, which is a continuation-in-part of Ser. No. 461,298, April 16, 1974, abandoned.

[51] Int. Cl.$^2$ .............................................. A61K 35/00
[52] U.S. Cl. .................................... 424/119; 424/115; 424/120; 424/121
[58] Field of Search ................ 424/115, 119, 120, 121

[56] References Cited

PUBLICATIONS

Derwent Farm Doc. No. 12766v/07, Abstracting Dutch patent 7,310,613, published 2-4-74.

Primary Examiner—Jerome D. Goldberg
Attorney, Agent, or Firm—Connolly and Hutz

[57] ABSTRACT

A species of Actinoplanes, designated *Actinoplanes auranticolor* ATCC 31011, when subjected to submerged aerobic fermentation under controlled conditions, produces a mixture of antibiotics which includes a number of macrocyclic lactones and depsipeptides. The individual compounds exhibit significant antibiotic activity. The crude antibiotic mixture or combinations of a pure macrocyclic lactone and a pure depsipeptide demonstrate marked synergistic antibiotic activity. These antibiotics act as growth promotants in chicks and swine and are effective in the treatment of swine dysentery.

This mixture of antibiotics is also produced by a species of Actinoplanes designated *Actinoplanes azureus* ATCC 31157. In addition, this culture produces a mixture of heptaene antibiotics with antifungal properties.

5 Claims, 5 Drawing Figures

MIXTURE OF ANTIBIOTICS PRODUCED BY A SPECIES OF ACTINOPLANES

CROSS-REFERENCE TO RELTED APPLICATIONS

This application is a continuation-in-part of co-pending application Ser. No. 541,800, filed Jan. 17, 1975 now abandoned which in turn is a continuation-in-part of application Ser. No. 461,298, filed Apr. 16, 1974 now abandoned.

BACKGROUND OF THE INVENTION

The phenomenon of synergism has been extensively reported in antibiotic literature; The Journal of Antibiotics 25, No. 6, 371 (1972); J. Chem. Soc. 19C, 1653 (1966); Bull. Soc. Chim. Belg. 68, 716 (1959); J. Amer. Chem. Soc. 82, 4414 (1960); Tetrahedron Letters 2687 (1971); J. Antibiotics, Ser. A 14, 14 (1961); Nature 187, 598 (1960); J. Chem. Soc. 2286 (1960); Antimicrobial Agents & Chemotherapy 360-365 (1964); Tetrahedron Letters 4231-4238 (1966); and J. Chem. Soc. 19C, 1669-1676 (1966).

The new synergistic mixtures of antibiotics of the present invention join the family of other reported synergistic mixtures: mikamycin, pristinamycin, ostreogrycin, streptogramin, P.A. 114, vernamycin and virginiamycin.

SUMMARY OF THE INVENTION

This invention is concerned with a mixture of antibiotics produced by the submerged aerobic propagation of *Actinoplanes auranticolor* ATCC 31011 in aqueous nutrient media. This mixture, containing macrocyclic lactones and depsipeptides, may be separated and recovered from fermentation broth by solvent extraction, counter-current distribution, column chromatography or combinations thereof. The individual antibiotic components exhibit significant antibiotic activity. The crude antibiotic mixture or combinations of a pure macrocyclic lactone and a pure depsipeptide obtained from the crude mixture demonstrate marked synergistic antibiotic activity. The crude antibiotic mixture and mixtures of pure macrocyclic lactones and depsipeptides, preferably Compounds 36,926 and 37,277, are effective chick and swine growth promotants and therapeutic agents in the control of swine dysentery.

This mixture of antibiotics is also produced by *Actinoplanes azureus* ATCC 31157 which, in addition, produces a mixture of heptaene antibiotics with antifungal properties.

DETAILED DESCRIPTION OF THE INVENTION

*A. auranticolor*, useful for the preparation of the antibiotics of this invention, was isolated from a soil sample in Egypt. It was grown on potato-carrot agar and found to belong to the class of actinomycetes producing sporangia like those of the genus Actinoplanes. It was grown, therefore, on a number of media used for the study of this genus and compared with *A. auranticolor* ATCC 15330. Suspensions of the cultures were prepared by crushing pieces of the cultures derived from agar slants in small tubes each containing about 0.2 ml sterile distilled water, rinsing out the contents and combining the contents with additional sterile water to make a volume of about 5 ml for each culture. These suspensions were used to plant the cultures in tubes, slants or petri dishes of the various media. The incubation temperature was 28° C. except where otherwise noted. Readings of results were made at intervals up to 22 days for some tests but most results were recorded after 14 days.

The colors of the cultures are those of Maerz and Paul, Dictionary of Colors, 2nd edition, 1950, as well as personal descriptive terms. The new cultures, Pfizer F. D. 24090 and 24561, were submitted to The Americann Type Culture Collection in Rockville, Maryland and given the designation *Actinoplanes auranticolor* ATCC 31011 and *Actinoplanes azureus* ATCC 31157, respectively. The permanency of the deposits and ready accessibility thereto by the public are afforded in the event the patent is granted. Access to the cultures is available during pendency of the application under Rule 14 and 35 USC 112. All restrictions on the availability to the public of the cultures deposited will be irrevocably removed upon granting of the patent.

Identification media used for the characterization of *A. auranticolor* and references for their composition are as follows:

1. 2% tap water agar.
2. Potato-Carrot Agar. M. P. Lechevalier, J. Lab. & Clin. Med. 71, 934–944 (1968). Use only 30 g potatoes and 2.5 g. carrots but 20 g. agar.
3. Czapek-Sucrose Agar. waksman, S. A., The Actinomycetes 2, (1961) Medium No. 1, p. 328.
4. Glucose-Asparagine Agar. Waksman, as above, Medium No. 2, p. 328.
5. Yeast Extract-Malt Extract Agar. Antibiotics Ann. 1956/1957, pp. 947–953.
6. Hickey and Tresner Agar. J. Bact. 64, 891–892 (1952).
7. Potato-Glucose Agar. Peel, cut up and steam 100 g. potatoes in 500 ml water, filter through cheese cloth, add 10 g. glucose, 20 g. agar and enough water to make one liter.
8. Starch Agar. J. Bact. 73, 15–27 (1957).
9. Gelatin. J. Bact. 73, 15–27 (1957).
10. Tyrosine Agar. J. Bact. 147–150 (1955).
11. Difco Peptone Iron Agar.
12. Difco Skim Milk.
13. Dextrose Nitrate Broth. Waksman, S. A., The Actinomycetes 2, 328 (1961). Medium No. 1 with 3.0 g. glucose in place of sucrose and without agar.
14. Organic Nitrate Broth. J. Bact., 73, 15–27 (1957).
15. ATCC Medium 172. American Type Culture Catalogue, 10th edition, p. 235 (1972).
16. Carbon Utilization. J. Bact., 56, 107–114 (1948).

The description of this new culture is as follows:

Tap Water Agar — growth poor, thin, flat, near 9D2 (very pale pink); no aerial mycelium; substrate mycelium colorless to 9D2; no soluble pigment.

Czapek-Sucrose Agar — growth moderate to good, flat, near 9G6 (pale orange); no aerial mycelium; substrate mycelium near 9G6; no soluble pigment.

Glucose-Asparagine Agar — growth moderate, raised, roughened, near 9L9 (light orange); no aerial mycelium; no soluble pigment.

Yeast Extract-Malt Extract Agar — no growth.

Hickey and Tresner Agar — growth moderate to good, slightly raised and roughened, near 9F9 (dull orange); faint whitish bloom on surface; substrate mycelium near 9I8; pale brownish soluble pigment.

Potato-Glucose Agar — growth moderate, raised, roughened, near 9L9 (light orange); no aerial mycelium; substrate mycelium near 9L9; no soluble pigment.

Tyrosine Agar — growth poor to moderate, flat, near 13A10 (dull reddish orange); no aerial mycelium; substrate mycelium near 10D11; brown soluble pigment.

Gelatin — growth moderate, flat, near 9K12 (reddish orange); trace of whitish bloom; substrate mycelium near 9K12; no soluble pigment.

Starch Agar — growth moderate to good, raised, near 9K10 (orange); light whitish bloom; substrate mycelium near 9K10; pale yellow soluble pigment.

Starch was weakly hydrolyzed; gelatin liquefaction was strong; nitrates were not reduced to nitrites in either nitrate medium even in 22 days (growth was very poor in dextrose nitrate broth but good in organic nitrate broth); hydrogen sulfide was weakly produced; there was no soluble pigment in peptone iron agar; there was no coagulation or hydrolysis of milk even in 22 days; tyrosine was not digested; growth on ATCC Medium 172 occurred at 21° to 37° C. with best growth at 28° and 37° C.; there was no growth at 45° C. Arabinose, fructose, glucose, mannitol, raffinose, rhamnose, sucrose and xylose were utilized; inositol was not utilized. There was no odor on any medium.

Sporangia were produced only on the potato-carrot agar. They formed a palisade layer. Measurements were 5.5–11 × 4.5–8 microns in width and breadth and 9–12 microns in height. They were quite numerous, irregular in shape and set spores free by gradual softening. Sporangia from potato-carrot agar after three weeks incubation released spores in a few hours at about 21° C. when pieces of the growth were submerged in a small amount of a solution of 1 gram of glucose and 1 ml of Tween 80 in 1 liter of water (a modification of a solution used by M. L. Higgins, J. Bact. 94, 495–498, 1967). The spores were in chains of irregular shape in the sporangia but when set free were subglobose and 1.6 microns wide to broadly elliptical, 1.6–2.2 × 1.1–1.6 microns. Almost all were motile.

*A. auranticolor* ATCC 15330 and the new strain *A. auranticolor* ATCC 31011 looked essentially alike in morphological traits, color and soluble pigment on Bennett's Agar, Nutrient Agar, Yeast Extract Agar, Glucose-Asparagine Agar, Glycerol-Asparagine Agar, Calcium Malate Agar and Tyrosine Agar.

Neither culture reduced nitrate to nitrite; both produced hydrogen sulfide weakly and failed to produce melanin on peptone-iron agar; both hydrolyzed starch. *A. auranticolor* ATCC 15330 caused no change in skim milk tubes whereas the new culture caused clearing in three of the six tubes of milk used and after 21 days produced a yellow-cream soluble pigment.

*A. auranticolor* ATCC 31011 utilized glucose, arabinose, fructose, mannitol, raffinose, rhamnose, sucrose and xylose. *A. auranticolor* ATCC 15330 utilized all these sugars with the exception of raffinose. Sporangia and spores of the two cultures were similar with the spores of *A. auranticolor* ATCC 15330 more rod shaped.

Most importantly, *A. auranticolor* ATCC 15330 did not produce any antibiotic activity under the fermentation conditions in which *A. auranticolor* ATCC 31011 produced the mixture of antibiotics of the present invention.

The lyophilized culture of *A. azureus* ATCC 31157 was inoculated into flasks of ATCC Medium 172 (liquid), grown four days, centrifuged, washed with water and resuspended in water to give a suspension which was used for planting.

The references for the media and description of results are given below. The capitalized names of colors are those of Ridgway's *Color Standards and Nomenclature.*

Bennett's Agar (Waksman, *The Actinomycetes* Vol. II, medium no. 30, p. 331, 1961): growth good, raised, roughened, cream color but spotted or sometimes almost completely near Porcelain Blue to Gobelin Blue; reverse similar to surface in color; soluble pigment pale-yellow; no special odor.

Nutrient Agar (Waksman, *The Actinomycetes* Vol. II, medium no. 14, p. 330, 1961): growth poor to moderate, flat, Pinkish-Cinnammon; reverse similar to surface in color; soluble pigment yellow; no odor.

Yeast-Extract Malt-Extract Agar (Pridham et al., *Antibiotics Ann.* 1956/57, pp. 947-953, 1957): growth good, raised, roughened, some of growth cream colored but almost all of surface Deep Delft Blue; reverse greenish-blue; soluble pigment pale yellow; no odor.

Czapek-Glucose Agar (Waksman, *The Actinomycetes,* Vol. II, medium no. 1 p. 328, 1961 with 30.0 g glucose substituted for sucrose): growth moderate in isolated, heaped masses, cream colored; reverse same color as surface; no soluble pigment; no odor.

Glucose-Asparagine Agar (Waksman, *The Actinomycetes,* Vol. II, medium no. 2, p. 328, 1961): growth good, cream colored, spotted or sometimes almost completely near Porcelain Blue to Gobelin Blue; reverse similar to surface in color; soluble pigment pale-yellow; no special odor.

Glycerol-Asparagine Agar (Waksman, *The Actinomycetes,* Vol. II, medium no. 3, p. 328, 1961): growth good, slightly raised, Cadmium Orange with minute spots near Porcelain Blue in color in central part of streaks; reverse similar to surface in color; soluble pigment pale-yellow; no odor.

Calcium Malate Agar (Waksman, *Bacteriological Reviews* 21: 1–29, 1957): growth barely visible, flat, thin, colorless; reverse not visible; no soluble pigment; no digestion of malate; no odor.

Tyrosine Agar (Gordon and Smith, *Jr. Bact.* 69; 147-150, 1955): growth moderate, flat, Fuscous; reverse like surface in color; soluble pigment dark brown; tyrosine digested; no odor.

Difco Skim Milk: even in 22 days no coagulation, no clearing, no soluble pigment.

Dextrose Nitrate Broth (Waskman, *The Actinomycetes,* Vol. II, medium no. 1, p. 328, 1961 with 3.0 g of glucose substituted for sucrose and without agar) even after 22 days no reduction of nitrate to nitrite.

Organic Nitrate Broth (Gordon and Mihm, *Jr. Bact.* 73: 15–27, 1957): even in 22 days no reduction of nitrate to nitrite.

Difco Peptone Iron Agar Slants with Lead Acetate Strips in Mouths of Tubes: slight darkening of lead acetate strips in only three days, black soluble pigment in three days.

Starch Agar (Gordon and Mihm, *Jr. Bact.* 73: 15–27, 1957): moderate zone (7 mm) of hydrolysis in seven days.

Carbon Utilization (Pridham and Gottlieb, *Jr. Bact.* 56: 107-114, 1948): utilized glucose, fructose, inositol, mannitol, raffinose and sucrose; did not utilize arabinose, rhamnose or xylose.

Sporangia and Spores: no sporangia were found on any of the first eight media in petri dishes after 14 days of growth, but when the culture was streaked on a medium of a filtrate of 30 g peeled potatoes and 2.5 g of peeled carrots that were boiled until cooked, filtered through cheesecloth, supplemented with 20 g agar and volume adjusted to one liter (based on medium of M. P. Lechvalier, *Jr. Lab. and Clinical Med.* 71: 934–944, 1965) it produced sporangia in 14 days.

The sporangia were fairly numerous, in a palisade layer, approximately round but surface rough; provided with short stalks; sporangia 5–6 microns and round to 5.5–6.5 × 4.5–5.5 microns.

Spores from this medium were short rods but non-motile. However, spores from a three-week old culture on Bennett's Agar in a water preparation did, after 10–15 minutes, begin to break open the sporangia and emerge as very active, motile cells. The spores were mostly short rods, 1.6 × 1.1 microns but sometimes nearly round and about 1.5 microns wide.

Because *A. azureus* ATCC 31157 produces a mixture of heptane antibiotics which appear to be similar to or indistinguishable from those produced by *A. caeruleus* NRRL 5325 as reported in Program and Abstracts 14th Interscience Conference on Antimicrobial Agents and Chemotherapy (1974) and Antimicrobial Agents & Chemotherapy 7, 457 (1975), cultural and morphological comparisons of the two cultures were made. In the following tables, only the ways in which the two cultures were obviously different are listed.

| Medium | A. azureus | A. caeruleus NRRL 5325 |
|---|---|---|
| Tryptone Yeast - Extract Broth | Brown soluble pigment in two days | No soluble pigment even in seven days |
| Peptone Iron Agar Slants with Lead Acetate Strips | Slight Production of hydrogen sulfide by seventh day | Slight production of hydrogen sulfide by third day but no increase thereafter |
| Skim Milk | No coagulation or clearing even in 21 days | Coagulation in all six tubes in 21 days; partial peptonization in half of tubes |
| Dextrose Nitrate Broth | No production of nitrite even in 24 days | Production of nitrite in two days |
| Organic Nitrate Broth | " | " |
| Glucose - Asparagine Agar | Growth near Terre Verte; no soluble pigment | Growth near Pinard Yellow; pale yellow soluble pigment |
| Glycerol - Aspargine Agar | Growth orange at tips of streaks, Antique Brown to Slate Color in older parts of streaks; no soluble pigment | Growth Ochraceous Orange at tips of streaks, Artemisia Green in order parts of streaks; yellow soluble pigment |
| Bennetts' Agar | Growth Warm Buff at tips of streaks, near Celandine Green in older parts of streaks | Growth near Ochraceous Buff |
| Yeast Extract - Malt Extract Agar | Growth Green-Blue Slate to Dark Green-Blue Slate | Growth Warm Buff but with Celandine Green to Artemisia Green color in older parts of streaks |
| Nutrient Agar | Growth near Cinnamon-Rufous | Growth near Ochraceous Buff |
| Tyrosine Agar | Growth near Blackish Brown 3 | Growth Russet |
| Starch | Growth near Hazel to Ferruginous | Growth Orange around edge, whitish bloom over rest of streak |

The last seven media were incubated longer for a total of 21 days. The final results were the same as recorded above after 14 days.

| Carbohydrate Utilization | A. azureus | A. caeruleus NRRL 5325 |
|---|---|---|
| Mannitol | ± | ++ |
| Rhamnose | − | ++ |
| Fructose | + | ++ |
| Inositol | + | ++ |

Sporangia - on weak Potato-Carrot Agar sporangia were the same in size and shape, but the number produced by *A. caeruleus* NRRL 5325 was much greater than the number produced by *A. azureus*. Of the media that seemed likely to have sporangia, Calcium Malate Agar, Tap Water Agar and Yeast Extract-Malt Extract Agar did not show production of sporangia by either culture Cultivation of the Actinoplanes cultures preferably takes place in aqueous nutrient media at a temperature of 28°–36° C., and under submerged aerobic conditions with agitation. Nutrient media which are useful for such purposes include a source of assimilable carbon such as sugars, starch and molasses; a source of organic nitrogen such as casein, enzymatic digest of casein, soybean meal, cottonseed meal, peanut meal and wheat gluten. A source of growth substances such as distillers' solubles, fish meal and yeast extract as well as slats such as sodium chloride and calcium carbonate and trace minerals such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about one half to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic mixture may be obtained by employing growth from a slant of the culture on a medium such as ATCC Medium 172 to which previous reference was made. The growth may be used to inoculate either shake flasks or inoculum tanks, or alterantively, the inoculum tanks may be seeded from the shake flasks. In shaken flasks growth will generally have reached its maximum in about 4 days whereas inoculum in submerged inoculum tanks will usually be at the most favorable period in 2 to 3 days. Substantial antibiotic activity is obtained in the final fermentor stage in approximately 20 to 30 hours.

The process of antibiotic production is conveniently followed during fermentation by biological assay of the broth employing a sensitive strain of *Staphylococcus aureus*. Standard plate assay technique is employed in which the zone of inhibition surrounding a fliter paper disc saturated with the broth is used as a measure of antibiotic potency. After the fermentation broth has reached a desired level of antibiotic potency, the products are isolate from either whole broth or filtered broth. In the latter case, the mycelium is removed by filtration or centrifugation. Various types of equipment such as filter presses, centrifuges, etc. may be employed.

Thin layer chromatography employing silica gel is a useful tool for analyzing the antibiotic mixture produced in fermentation media and the composition of crude and purified materials extracted from fermentation broths. The resolution of the components of the antibiotic mixture is importantly dependent on antibiotic loading of the system. Too little antibiotic potency fails to reveal minor antibiotic components; too much antibiotic potency results in a dragging effect with resulting poor resolution.

The developing system for the thin layer chromatography is chloroformethanol (9:1). The thin layer chromatograms, after development, may be observed under ultaviolet light at 254 m$\mu$ and 366 m$\mu$. Bioautographic detection of the antibiotic components may be accomplished by means of an overlay of a thin layer of nutrient agar seeded with a sensitive strain of *Staphylococcus aureus or other sensitive organism.*

The primary components in the antibiotic mixture produced by *A. auranticolor* ATCC 31011 and *A. azureus* ATCC 31157 include a number of macrocyclic lactone and depsipeptide antibiotic components. The appearance of non-appearance or percentage composition of these components varies from fermentation to fermentation and is a function of time, pH, media composition, etc. Under sets of conditions given in the examples hereinafter, major antibiotic components in the antibiotic mixture are Compounds 37,277 (depsipeptide) and 36,926 (macrocyclic lactone) while the minor antibiotic components are Compounds 37,932 and 40,042 (depsipeptides) and 35,763 (macrocyclic lactone).

The components of the antibiotic mixture may be separated and recovered from fermentation broth by a number of different procedures including solvent extraction, Craig counter-current distribution, column chromatography or combinations thereof. Various organic solvents such as chloroform, ethyl acetate and methyl isobutyl ketone are useful in extracting the antibiotics from broth. Solvent extraction is preferably carried out by twice extracting the broth at about pH 7 with a volume of solvent approximately equal to about one third to one half the volume of broth from which it is desired to recover the antibiotic mixture. Depending on volumes of broth involved, various pieces of equipment such as separatory funnels, stirred tanks and mechanical extracting devices such as centrifugal separators are helpful for extraction purposes.

The preferred method of separation and recovery of the components of the antibiotic mixture is as follows: either whole or clairified broth is adjusted to about pH 7 and twice extracted with about one third to one half volume of methyl isobutyl ketone. The solvent extract is concentrated under vacuum and the concentrate defatted by extraction with heptane or petroleum ether. The defatted solvent concentrate is then taken to dryness under vacuum. The solids are subjected to Craig counter-current distribution (6 plates) utilizing toluene, 5 parts: ethanol, 2 parts: aqueous phosphate buffer, pH 4.5, 3 parts. The separated layers furnish the upper and lower of the counter-current distribution system. After distribution, the layers are monitored by thin layer chromatography. The separated fractions are taken to dryness under vacuum.

The solids containing the depsipeptides are dissolved in chloroform, treated with activated charcoal, filtered and evaporated in vacuo. The residue obtained on evaporation of the chloroform is dissolved in acetone. The solids precipitated by the addition of heptane are dissolved in a small amount of chloroform and applied to a column of silica gel made up in chloroform:n-propanol (99:1% — v/v). The column is developed with the same solvent system under 80 psi. The column cuts are monitored by thin layer chromatography. The cuts containing separated depsipeptides are combined, evaporated in vacuo and crystallized from acetone-heptane.

The counter-current fractions containing the macrocyclic lactones are combined, evaporated in vacuo and the solids taken up in ethyl acetate. The solution is stirred with silica gel, filtered and the solvent removed in vacuo. The residue is taken up in ethyl aectate and precipitated with hexane. The solids are dissolved in a small amount of chloroform and chromatographed under 80 psi on a pH 6.0 buffered silica gel column made up in ethyl acetate. The developing system is ethyl acetate-tetrahydrofuran-hexane (80:20:20) saturated with aqueous pH 6.0 phosphate buffer. The column cuts are monitored by thin layer chromatography. The cuts containing separated macrocylic lactones are combined and evaporated in vacuo. The individual fractions are separately worked up by further Craig counter-current distribution and/or column chromatography utilizing different developing systems. Careful monitoring at every purification stage locates the individual macrocyclic lactones sufficiently isolated so that the solvent fractions can be taken to dryness to yield the pure compounds.

*A. auranticolor* ATCC 31011 and *A. azureus* ATCC 31157 produce at least four depsipeptides and at least four macrocyclic lactones. However, the primary components are the depsipeptides Compounds 37,277 (major), 37,932 (minor), 40,042 (minor), and the macrocyclic lactones Compounds 36,926 (major) and 35,763 (minor).

Crude antibiotic mixtures obtained directly from broth and purified individual components possess wide antibacterial spectra. Among the organisms failing to propagte in the presence of the antibiotics are *Salmonella typhos, Shigella dysenteriae, Escherichia coli, Klebsiella pneumoniae, Staphylococcus aureus, Streptococcus* pyogenes, Streptococcus faecalis, Diplococcus pneumoniae, Bacillus substilis, Cornynebacterium diphtheriae, Clostridium septicum, Brucella abortus, Neisseria sicca, Lactobacillus acidophilus and Pasteurella multocida.

The antibiotics of this invention, either as a crude mixture or in the form of the purified individual components or mixtures thereof, may be employed in the treatment of various infections in man and animals. In general, these antibiotics are most desirably administered in daily oral doses of 0.5–1 gram or parenteral doses of 100 to 500 mg., depending on the type and severity of the infection and weight of the subject being treated.

The compounds of this invention may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinylpyrrolidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspensions and/or elixirs are desired for oral administration, the essential active ingredient therein may be combined with various sweetening of flavoring agents as well together with such diluents as water, ethanol, propylene glycol, glycerol and various combinations thereof.

Solutions of these antibiotics in sesame or peanut oil or in aqueous propylene glycol may be employed for parenteral administration.

It is of interest that the individual antibiotics of this invention exhibit antimicrobial activity which is largely bacteriostatic in nature. However, crude antibiotic mixtures or mixtures of a purified depsipeptide and a purified macrocyclic lactone exhibit synergistic activity which is largely bactericidal in nature.

When major macrocyylic lactone Compound 36,926 (A) and major depsipeptide Compound 37,277 (B) were assayed individually and in combination by the tube dilution method versus the following organisms, the following minimal inhibitory concentrations in micrograms/ml (M.I.C.) were found:

| Organism | A | B | A + B | Crude Mixture |
|---|---|---|---|---|
| Staph. aureus 005 | 1.56 | 25 | 0.10 | <0.10 |
| Staph. aureus 005 | 3.12 | 12.5 | 0.78 | <0.10 |
| Strep. faecalis | 100 | 12.5 | 1.56 | 0.20 |
| Neisseria sicca | 0.39 | 50 | 0.10 | <0.10 |
| Treponema hyodysenteriae | — | — | — | 0.19 |
| Strep. pyogenes | 0.39 | 12.5 | 0.10 | <0.10 |

| Organism | A | B | A + B | Crude Mixture |
|---|---|---|---|---|
| Bacteroides fragilis 35614 | 25 | 50 | 0.78 | 0.78 |
| Clostridium innocuum | 6.25 | >100 | 0.20 | 0.39 |
| Lactobacillus casei var. casei | 3.12 | 6.25 | 0.20 | 0.39 |

Comparable results were obtained when minor macrocyclic lactone Compound 35,763 (A')and minor depsipeptide Compound 37,932 (B') were assayed individually or in appropriate combinations, i.e. A'≦ A, B'≦ B while (A' + B') ≦ (A' + B) ≦ (A + B') ≦ (A + B). Maximum synergistic activity of combinations of purified macrocyclic lactone and depsipeptide is obtained over a range of about a ratio of 1–2:1. Approximately such ratios occur in fermentations broths of $A.$ $auranticolor$ ATCC 31011 and $A.$ $azureus$ ATCC 31157 and in crude antibiotic mixtures isolated therefrom. This finding is in contrast to other reported synergistic antibiotic mixtures where the synergistic factors occur in fermentation broths and crude mixtures at sub-optimal ratios.

In vivo protection data provided by oral and subcutaneous administration in mice experimentally infected with a strain of Staphylococcus aureus are shown in Table I.

Table I

| | PD$_{50}$ Values (mg/kg) | |
|---|---|---|
| | S. aureus 01A005 | |
| | Oral | Subcutaneous |
| Compound 36,926 | > 200 | > 200 |
| Compound 37,277 | > 200 | > 200 |
| Compounds 36,926 + 37,277(1:1) | 210 | 60 |
| Crude antibiotic mixture (Lot 1, p.23) | 150–200 | 72–120 |

The antibiotics of the present invention may be regarded to be of special interest as growth promotants in poultry and animals because of their wide antibacterial spectra and for the treatment of swine dysentery because of marked activity against Treponema hyodysenteriae, an anaerobic spirochete implicated in this disease.

The growth promoting activity of a crude antibiotic mixture (Lot 1, p. 24) was determined in young feeder pigs in a 40-day trial. Average daily gain, feed consumption and efficiency were significantly improved (p < 0.01) over the non-medicated control (Table II).

Table II

| Treatment | Average Daily Gain (kg) | Average Daily Feed (kg) | Feed Efficiency* |
|---|---|---|---|
| Non-medicated | 0.35 | 0.91 | 2.57 |
| Lot 1, (p. 23) 50 ppm | 0.63 | 1.35 | 2.15 |

*lbs. of feed per lb. of weight gain

Comparable results may be obtained with the other crude antibiotic mixtures of the compositions described on page 24 over a range of 10 to 100 ppm, 20 to 200 ppm of Compound 36,926, and 10 to 100 ppm of Compound 36,926 with Compound 37,277 and/or Compound 37,932

Growth promoting efficacy was demonstrated in a chick battery feed trial. Significant improvements (p < 0.01) in weight gains over the non-medicated controls were observed for the chicks on an antibiotic-feed diet (Table III).

Table III

| Treatment | Average Weight Gain (grams) | Average Feed Consumed (grams) | Feed Efficiency |
|---|---|---|---|
| Non-medicated | 566 | 939 | 1.66 |
| Lot 1, (p. 23) 10 ppm | 608 | 949 | 1.56 |

Comparable results may be obtained with the other crude antibiotic mixtures of the compositions described on page 24 over a range of 10 to 100 ppm, 20 to 200 ppm of Compound 36,926, and 10 to 100 ppm of Compound 36,926 with Compound 37,277 and/or Compound 37,932

The prophylactic efficacy of the antibiotics of this invention was determined in swine experimentally infected with infectious material causing swine dysentery. Colonic content and mucosal scrapings were obtained from a clinically diagnosed field outbreak of swine dysentery. Normal pigs were infected with this material by direct inoculation. Antibiotic-containing feed was administered over a 28 day period. The results are shown in Table IV.

Table IV

| Treatment | | Morbidity (%) | Mortality (%) | Average Daily Gain (kg) |
|---|---|---|---|---|
| Non-medicated | | 100 | 40 | − 0.13 |
| Lot 1, (p. 23) | 50 ppm | 0 | 0 | 0.66 |
| | 37.5 ppm | 0 | 0 | 0.57 |
| | 25 ppm | 0 | 0 | 0.68 |
| | 12.5 ppm | 0 | 0 | 0.61 |
| | 6.25 ppm | 50 | 10 | 0.47 |

Comparable results may be obtained over a range of 10 to 100 ppm with the other antibiotic mixtures of page 24, 20 to 200 ppm of Compound 36,926, and 10 to 100 ppm of Compound 36,926 with Compound 37,277 and/or Compound 37,932.

EXAMPLE I

A sterile aqueous medium having the following composition is prepared:

| | Grams/liter |
|---|---|
| Glucose | 10.0 |
| Soluble starch | 20.0 |
| Yeast extract | 5.0 |
| Enzymatic digest of casein | 5.0 |
| CaCO$_3$ | 1.0 |
| pH - 7.0 | |

Cells from a slant of *A. auranticolor* 31011 or *A. azureus* 31157 on ATCC medium 172 are transferred to a series of 300 ml-Erlenmyer flasks each containing 50 ml of this medium and shaken on a rotary shaker for 3–4 days at 28°–30° C. Aliquots of 5 ml of the grown inoculum are transferred to 300 ml-Erlenmyer flasks each containing 100 ml of the sterile medium described above. After shaking for 3–4 days at 28°–30° C., 5–10% v/v of the grown inoculum is transferred to a four liter fermentor containing two liters of the following sterile medium:

| | Grams/liter |
|---|---|
| Yeast extract | 2.0 |
| Glucose | 10.0 |
| Corn Steep Liquor | 1 ml |
| Enzymatic digest of casein | 5.0 |
| Cobalt Chloride | 0.002 |
| pH - 7.0 | |

The fermentation is conducted for 20 to 30 hours at 28°–36° C. with stirring at 1700 revolutions/minute and aeration at about one volume of air per volume of broth per minute.

The whole broth is adjusted to pH 7 if necessary, and twice extracted with one third to one half volume methyl isobutyl ketone. The solvent extract is concentrated under vacuum and defatted by extraction with petroleum ether. The activity in the broth, solvent extract and subsequent fractions is followed by silica gel thin layer chromatography using a developing system of chloroform-ethanol (9:1) and observation under ultraviolet light at 254 and 366 m$\mu$.

The defatted solvent concentrate is taken to dryness under vacuum. The solids are subjected to a 6 plate Craig counter-current distribution utilizing toluene, 5 parts: ethanol, 2 parts: aqueous phosphate buffer, pH 4.5, 3 parts. The separated layers furnish the upper and lower phases of the counter-current distribution system. After distribution, the layers are monitored by thin layer chromatography.

Compound 37,277 is concentrated in the upper layer of plate O. Compound 37,932 is recovered from the upper layers of plates 1, 2 and 3. A third depsipeptide is derived according to the method of Example VI. The macrocyclic lactone Compound 35,763 is found primarily in the lower layers of plates 0 and 1. Compound 36,926 is concentrated in the lower phases of plates 2, 3, 4 and 5.

The upper phase of plate 0 containing Compound 37,277 is taken to dryness under vacuum, dissolved in chloroform and stirred for about 30 minutes with activated charcoal. The solution is filtered and evaporated in vacuo. The residue is dissolved in acetone and the solids precipitated by the addition of heptane. The precipitated solids are dissolved in a small amount of chloroform and chromatographed on a column of silica gel made up in chloroform: n-propanol (99.1% v/v). The column is developed with the same system under 80 psi. Column cuts are monitored by thin layer chromatography. The fractions containing separated Compound 37,277 are combined, evaporated in vacuo and the compound crystallized from acetone-heptane.

Compound 37,277 does not have a definitive melting point. Decomposition commences at 140–150° C. It is insoluble in diethyl ether, hexane, heptane and water. It is slightly soluble in acetone and benzene and readily soluble in methanol, ethanol, chloroform and methylene chloride.

Analysis of Compound 37,277 gives the following average proportions:

| | |
|---|---|
| Carbon | 60.91 |
| Hydrogen | 5.98 |
| Nitrogen | 10.45 |
| Oxygen (by difference) | 22.66 |

Compound 37,277 is optically active having a rotation of $[\alpha]_D^{25°} = +11°$ (c = 1.0, EtOH). Its ultraviolet light absorption maxima in ethanol occur at 225, 274, 282, 303 and 355 mμ with $E_{1\ cm}^{1\%}$ values of 309.3, 36.67, 45.01, 70 and 20, respectively.

Figure 1:
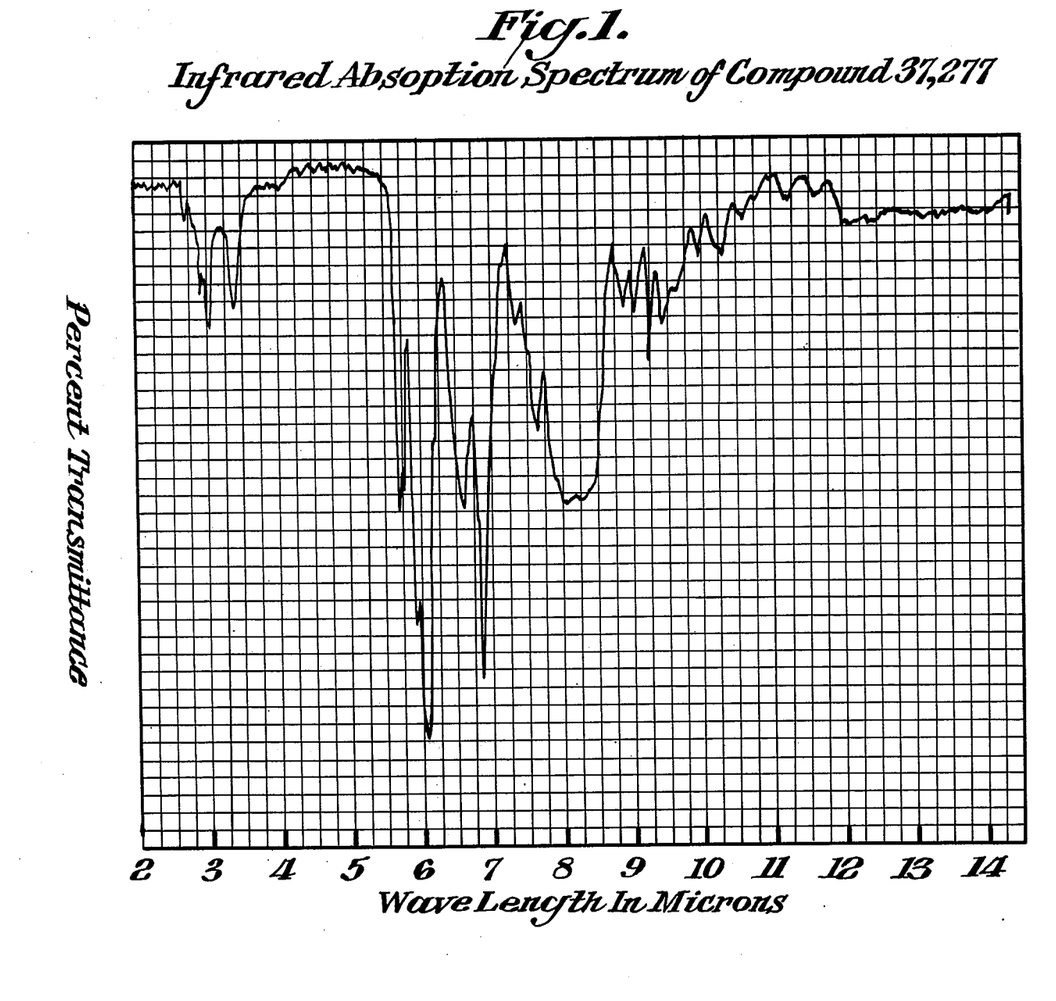

The infrared spectrum of Compound 37,277, FIG. 1, is attached. A chloroform solution shows characteristic absorption in the infrared region at the following wavelengths in microns: 3.05, 3.40, 5.70, 5.77, 5.93, 6.07, 6.62, 6.82 and 7.67.

The counter-current fractions containing Compounds 35,763 and 36,926 are evaporated in vacuo, the residue taken up in ethyl acetate and the solution stirred with silica gel. The filtered solution is evaporated in vacuo, the residue taken up with ethyl acetate and the solids precipitated by the addition of hexane. The precepitated solids are dissolved in a small amount of chloroform and chromatographed on a column of pH 6.0 buffered silica gel made up in ethyl acetate. The column is developed with ethyl acetate: tetrahydrofuran: hexane (80:20:20) saturated with aqueous pH 6.0 phosphate buffer under 80 psi. The first 17 column cuts each of 20 ml contain a yellow oil which is discarded. Cuts 26–40 are rich in Compound 36,926. Cuts 41–50 are largely a mixture of Compounds 36,926 and 35,763. Cuts 26–40 are combined, concentrated in vacuo and again chromatographed on silica gel with 20 ml cuts being collected. The first 15 cuts contain a yellow oil which is discarded. Cuts 16-30 are primarily Compound 36,926. Cuts 31–40 contain a mixture of Compounds 36,926 and 35,763. Cuts 16–30 are evaporated in vacuo, the residue dissolved in a small amount of chloroform and applied to a column of pH 6.0 buffered silica gel made up in chloroform. The column is developed with chloroform:ethanol (95.5:4.5% v/v) under 130 psi, and 160 cuts of 6 ml collected. The cuts 60-90 assay for only Compound 36,926. They are combined and evaporated in vacuo. The residue is dissolved in the minimum volume of ethanol and precipitated with ether to give pure, amorphous Compound 36,926.

Compound 36,926 is soluble in methanol, ethanol, chloroform and methylene chloride. It is insoluble in diethyl ether, hexane and heptane.

Compound 36,926 does not have a definitive melting point. Decomposition commences at about 100° C. Analysis gives the following average proportions:

| Carbon | 57.89 |
|---|---|
| Hydrogen | 6.78 |
| Nitrogen | 8.04 |
| Oxygen (by difference) | 27.29 |

The molecular weight by high resolution mass spectrum is 501, and the molecular formula $C_{26}H_{35}N_3O_7$.

Compound 36,926 is optically active having a rotation of $[\alpha]_D^{25°} = -130°$ (c = 1.0, EtOH). Its ultraviolet light absorption maximum in ethanol is 214 mμ with $E_{1\ cm}^{1\%}$ of 723.8.

Figure 2:
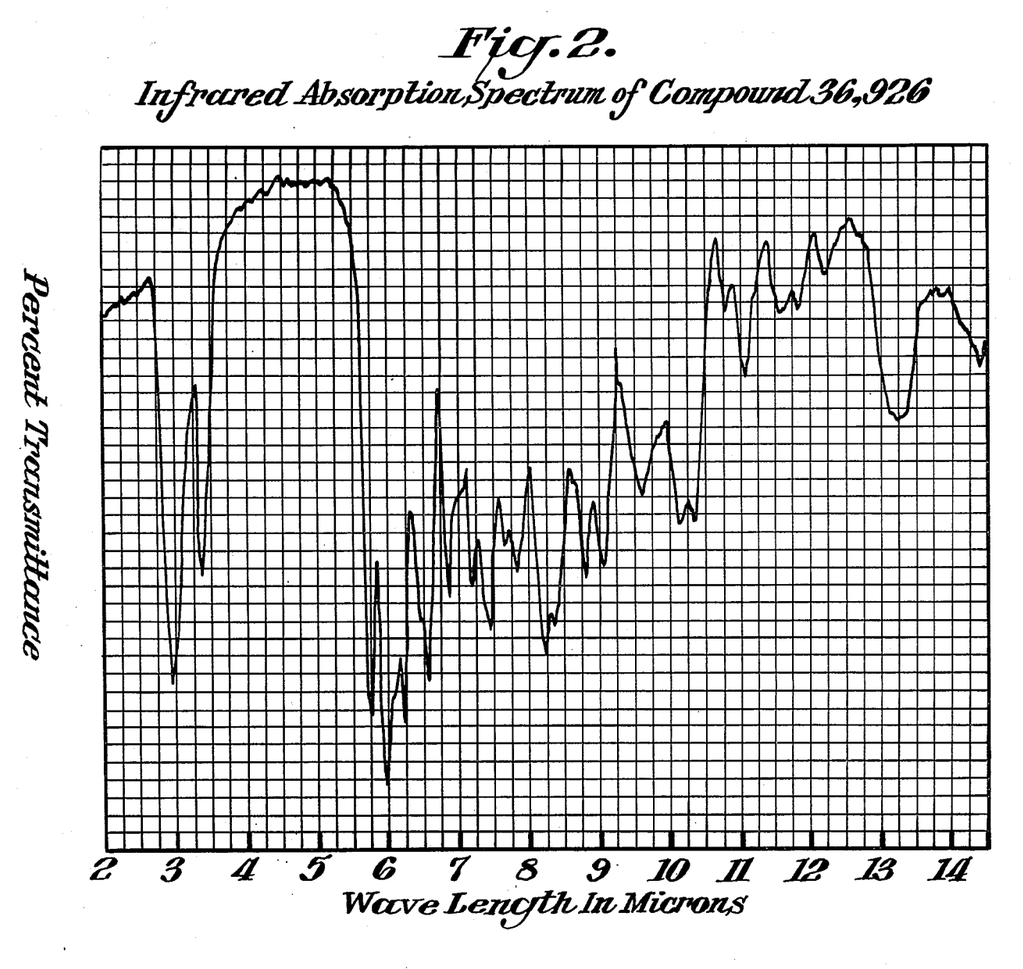

The infrared spectrum of Compound 36,926, FIG. 2, is attached. A KBr pellet shows characteristic absorption in the infrared region at the following wavelengths in microns: 2.95, 3.40, 5.75, 5.98, 6.23, 6.58, 6.87, 7.45, 8.25, 8.38, 8.80, 9.08, 10.15, 10.35, 11.10 and 13.30.

This compound may be similar to or indistinguishable from antibiotic A2315B reported at the Fourteenth Interscience Conference on Antimicrobial Agents and Chemotherapy, Sept. 11–13, 1974.

Compound 35,763 is isolated and purified in much the same way as Compound 36,926. The pure compound is soluble in methanol, ethanol, chloroform and methylene chloride. It is insoluble in diethyl ether, hexane and heptane. There is no definitive melting point. Decomposition commences at about 100° C. Analysis gives the following average proportions:

| Carbon | 61.29 |
|---|---|
| Hydrogen | 6.73 |
| Nitrogen | 8.83 |
| Oxygen (by difference) | 23.15 |

Molecular weight by high resolution mass spectrum is 503, and the molecular formula $C_{26}H_{37}N_3O_7$.

Compound 35,763 is optically active having a rotation of $[\alpha]_D^{25°} = -114°$ (c = 1.0, EtOH). Its ultraviolet light absorption maximum in ethanol is 218 mμ with $E_{1\ cm}^{1\%}$ of 668.9.

Figure 3:
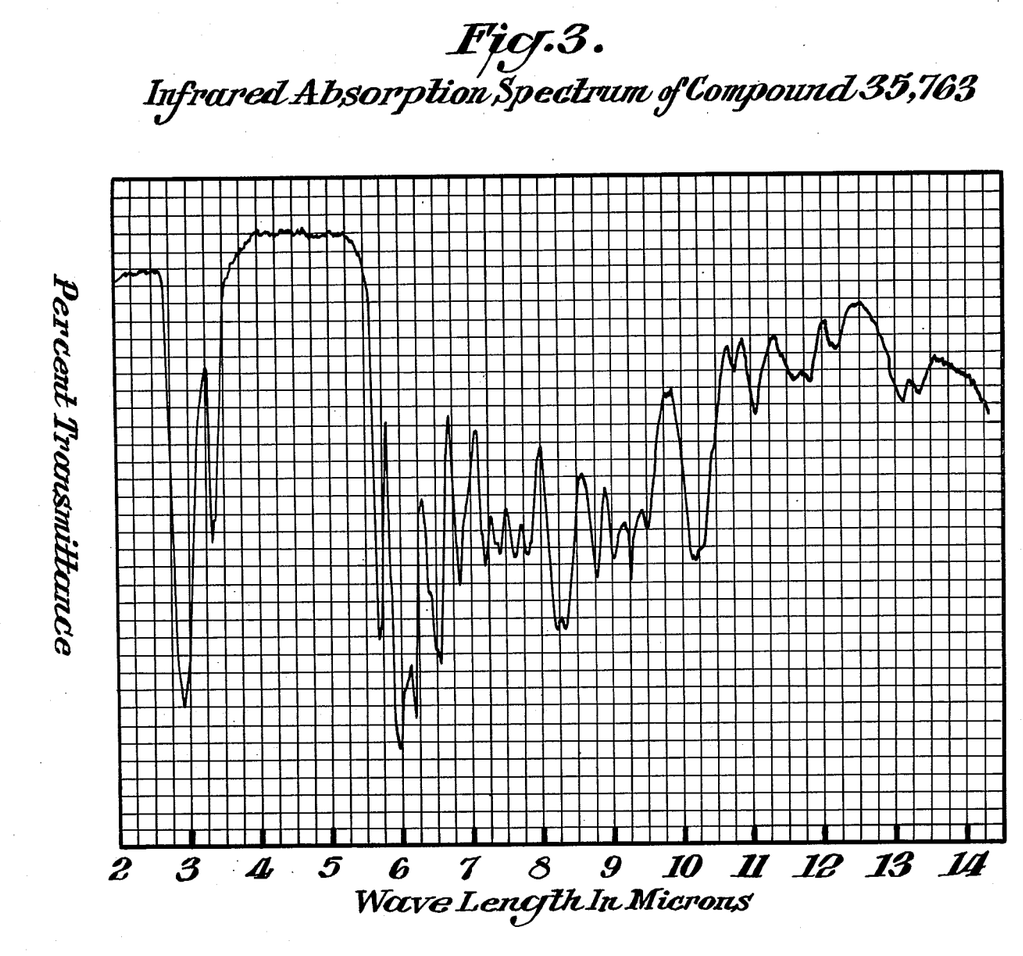

The infrared spectrum of Compound 35,763, FIG. 3, is attached. A KBr pellet shows characteristic absorption in the infrared region at the following wavelengths in microns: 2.95, 3.38, 5.73, 6.00, 6.23, 6.60, 6.88, 7.23, 8.25, 8.38, 8.83 and 10.20.

Compound 35,763 may be similar to or indistinguishable from antibiotic A-2315 described in Dutch Pat. No. 7,310,613.

The counter-current fractions containing Compound 37,932 were taken to dryness under vacuum, the residue triturated with petroleum ether and chromatographed on a silica gel column as described above. The appropriate fractions were combined and crystallized from acetone:heptane to afford Compound 37,932.

Compound 37,932 is soluble in methanol, ethanol, chloroform and methylene chloride. It is insoluble in diethyl ether, hexane, heptane and water. The compound does not have a definitive melting point. Decomposition commences at approximately 185° C. Elementary analysis gives the following average proportions:

| Carbon | 59.41 |
|---|---|
| Hydrogen | 6.01 |
| Nitrogen | 10.66 |
| Oxygen (by difference) | 23.92 |

Compound 37,932 is optically active having a rotation of $[\alpha]_D^{25°} = +5.0°$ (c = 0.25, CHCl$_3$). Its ultraviolet light absorption maxima in ethanol occur at 226, 276, 283, 305 and 355 mμ with $E_{1\ cm}^{1\%}$ values of 304.4, 36.8, 43.49, 70.25 and 20.07, respectively.

Figure 4:
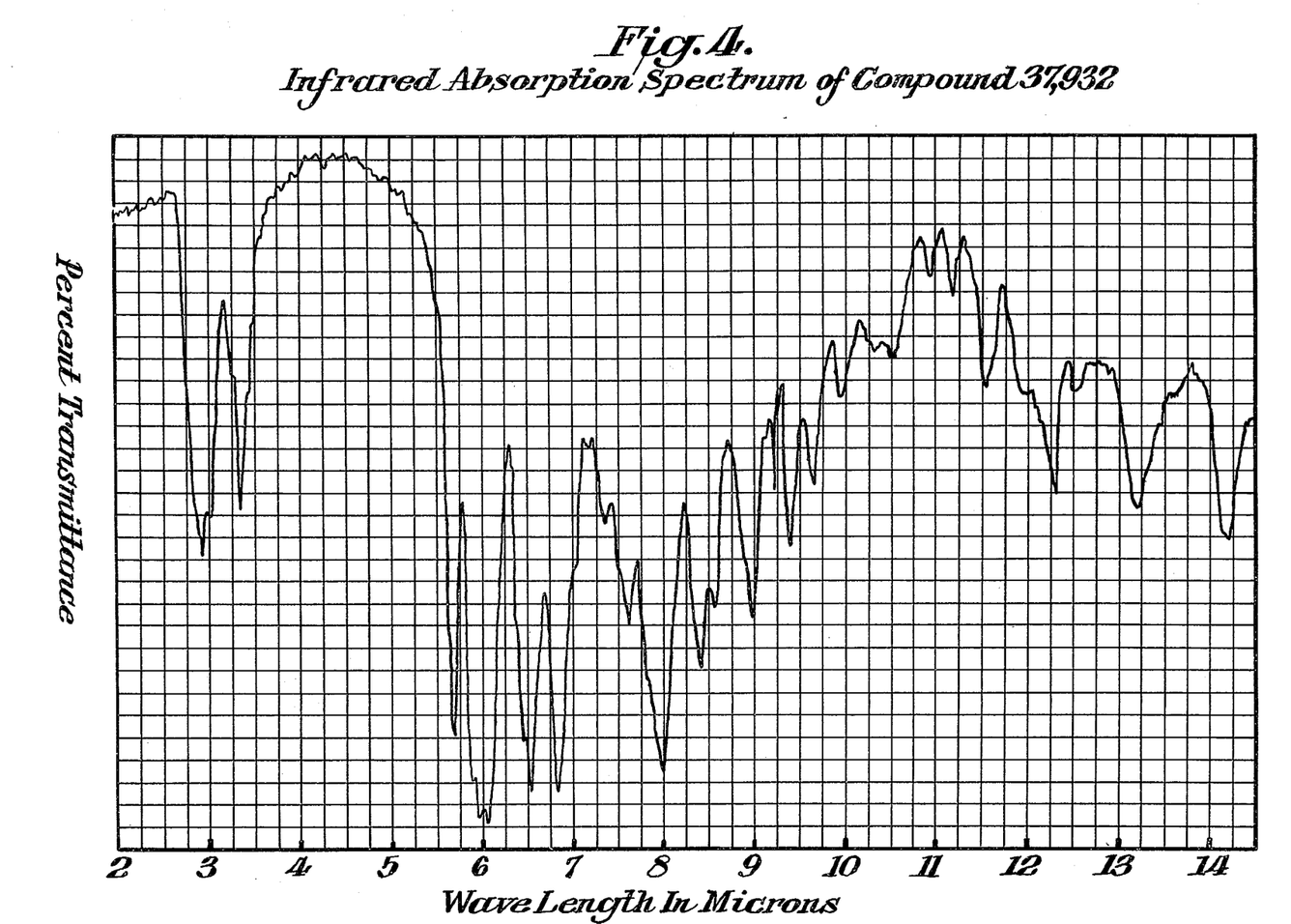

The infrared spectrum of Compound 37,932, FIG. 4, is attached. A KBr pellet shows characteristic absorption in the infrared region at the following wavelengths in microns: 2.96, 3.05, 3.38, 5.68, 5.73, 5.93, 5.98, 6.13, 6.50, 6.58, 6.88, 7.40, 7.65, 8.08, 8.45, 8.60, 9.03, 9.45, 9.70, 9.98, 10.55, 11.00, 11.25, 11.60, 12.35 and 13.25.

EXAMPLE II

The method of Example I may be repeated with comparable results employing a fermentation medium of the following composition:

|  | Grams/liter |
|---|---|
| Glucose | 8.0 |
| Tryptose | 3.0 |
| Enzymatic digest of casein | 1.0 |
| Glutamic acid | 1.0 |
| Soy flour | 0.5 |
| NaCl | 8.3 |
| $K_2HPO_4$ | 2.4 |
| $KH_2PO_4$ | 2.0 |
| $MnCl_2$ | 0.02 |

EXAMPLE III

The method of Example I may be repeated with comparable results employing a fermentation medium having the following composition:

|  | Grams/liter |
|---|---|
| Glucose | 10.0 |
| Soy flour | 10.0 |
| Corn steep liquor | 1 ml |

EXAMPLE IV

The method of Example I may be repeated with comparable results employing a fermentation medium having the following composition:

|  | Grams/liter |
|---|---|
| Molasses | 10.0 |
| Enzymatic digest of casein | 1.0 |
| Yeast extract | 2.0 |
| Corn steep liquor | 1 ml |
| Casein | 3.0 |

EXAMPLE V

The method of Example I was repeated. The methyl isobutyl ketone extract of the finished fermentation broth was taken to dryness under vacuum and the residue triturated with petroleum ether. The friable material was milled and the antibiotic components were quantitatively determined by high pressure liquid chromatogrphic assay. Representative bulk lots of crude antibiotic mixtures from separate fermentation runs assayed (percent) as follows:

| Lot No. | 35,763 | 36,926 | 37,932 | 37,277 | Misc. Components |
|---|---|---|---|---|---|
| 1 | 4.0 | 31.5 | 8.7 | 19.3 | 5.8 |
| 2 | 2.2 | 44.0 | 7.8 | 15.9 | 2.1 |
| 3 | .3.1 | 39.4 | 10.7 | 26.5 | 5.3 |
| 4 | 3.6 | 46.8 | 0.9 | 26.9 | 6.3 |
| 5 | 5.3 | 33.0 | 2.2 | 20.3 | 4.5 |
| 6 | 0.5 | 58.4 | 5.6 | 27.5 | 9.5 |
| 7 | 2.0 | 55.8 | 12.1 | 18.7 | 10.0 |

EXAMPLE VI

The method of Example I was repeated wherein the defatted solvent concentrate of the fermentation broth was subjected to column chromatography on silica gel $PF_{254}$ and silica gel 60 and development with chloroform:ethanol (98.2% v/v) with a subsequent three-tube Craig countercurrent distribution in a system of toluene:pH 4.5 aqueous potassium dihydrogen phosphate:ethanol (10:6:4 - v/v/v).

The purified fraction (5.93 grams) dissolved in chloroform was applied to a column (2.54 × 92 cm) of silica gel $PF_{254}$ made up in chloroform solution. The column was developed under 80 psi eluting with chloroform:n-propanol (99:1% v/v to 97:3% v/v to 94:6% v/v), 10 ml fractions collected which were assayed by silica gel thin layer chromatograms developed with $CHCl_3$-EtOH (90:10% v/v).

The appropriate fractions were combined and evaporated in vacuo. The residue was dissolved in acetone and stirred with activated charcoal (Darco KB) at room temperature for 30 minutes. After filtration and concentration in vacuo, the solid mass was crystallized from acetone:hexane as Compound 40,042.

Compound 40,042 does not have a definitive melting point. Decomposition commences at approximatey 160° C. It is soluble in acetone, chloroform and methylene chloride and insoluble in hexane, heptane and water.

Analysis of Compound 40,042 gives the following average proportions:

| Carbon | 61.08 |
|---|---|
| Hydrogen | 6.23 |
| Nitrogen | 10.75 |
| Oxygen (by difference) | 21.94 |

Compound 40,042 is optically active having a rotation of $[\alpha]_D^{25°} = -1.7°$ (c = 1.0, EtOH). Its ultraviolet light absorption maxima in ethanol occur at 230, 278, 282, 294, 303 and 355 m$\mu$ with $E_{1\,cm}^{1\%}$ values of 249.2, 69.77, 75.60, 89.10, 91.81 and 9.97, respectively.

Figure 5:
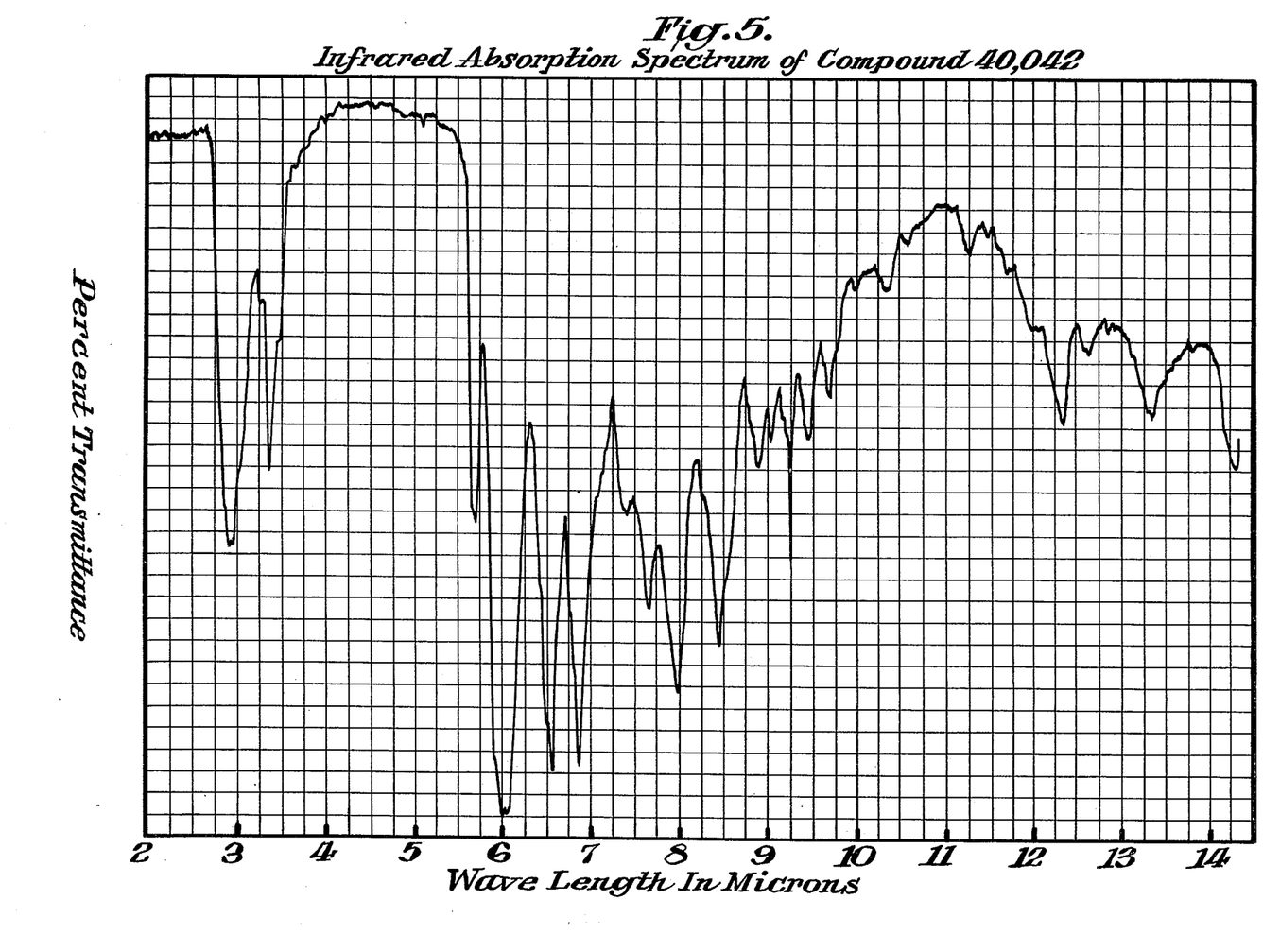

The infrared spectrum of Compound 40,042, FIG. 5, is attached. A KBr pellet shows characteristic absorption in the infrared region at the following wavelengths in microns: 2.92, 2.97, 3.37, 5.67, 5.70, 6.00, 6.58, 6.88, 7.68, 8.00, 8.47, 8.90, 9.04, 9.24, 9.47, 9.70, 12.35 and 13.37.

EXAMPLE VII

The methods of Example I and Example VI were repeated employing *A. azureus* ATCC 31157 in place of *A. auranticolor* ATCC 31011 to produce Compounds 36,926 37,277, 37,932, 40,042 and 35,763.

EXAMPLE VIII

The method of Example VII was repeated with filtered fermentation broth in place of whole broth. The separated wet mycelium was stirred with methanol, and the methanolic extract was concentrated to remove the solvent. The aqueous concentrate was extracted with n-butanol and the n-butanol removed in vacuo. The residue was partitioned between methyl isobutyl ketone and pH 9.0 phosphate buffer. Antifungal activity was followed by the use of *Candida albicans* as the test organism. The activity found in the lower aqueous phase was extracted into n-butanol after adjustment of the pH to 7.0. The solids derived on evaporation of the n-butanol were then chromatographed on silica gel 60 made up in chloroform:ethanol:water (4:7:1 - v/v/v). The sample was applied to the top of the column as a dispersion on silica gel 60 by the addition of a methanol slurry of the n-butanol solids to silica gel with removal of the methanol in vacuo. The column was developed with the system chloroform:ethanol:water (4:7:2 - v/v/v) and its progress monitored by silica gel chromatograms developed with n-butanol:acetic acid:-water:dioxane (6:2:1:1 -v/v/v/v) or chloroform: ethanol:-water (4:7:2 - v/v/v). The developed chromatograms were overlaid with a thin layer of agar seeded with *C. albicans*. The zones of inhibition were conveniently visualized by flooding the biooverlay with a 0.1% aqueous solution of 2,6-dichloroindolphenol sodium salt. The yeast active metabolites appeared as pale pink spots on a light blue background. Alternatively, spraying of the developed chromatograms with concentrated $H_2SO_4$:MeOH (1:1 - v/v) gave transient bright green spots on a white background which became grey on standing. Revealed were one major and at least three minor antifungal components. They were readily characterized as heptaenes by their ultraviolet light maxima in ethanol at 340, 358, 378 and 402 m$\mu$. The mixture of heptaenes appears to be similar to or indistinguishable from the heptaene mixture produced by the previously reported *A. caeruleus* NRRL 5325.

What is claimed is:

1. an antibiotic mixture produced by cultivating *Actinoplanes auranticolor* ATCC 31011 or *Actinoplanes azureus* ATCC 31157 under submerged aerobic conditions in an aqueous nutrient medium containing an assimilable source of carbon and nitrogen until substantial antibiotic activity is obtained.

2. Antibiotic substance Compound 37,277 which in crystalline form has an optical rotation of $[\alpha]_D^{25°} = +11°$ at a concentration of 1% in ethanol; absorption maxima in ethanol in the ultraviolet light region of the spectrum at 225, 274, 282, 303 and 355 m$\mu$ with $F_{1\ cm}^{1\%}$ values of 309.3, 36.67, 45.01, 70 and 20, respectively; having the average composition by weight of 60.91% carbon, 5.98% hydrogen, 10.45% nitrogen and 22.66% oxygen (by difference); and when dissolved in chloroform exhibiting characteristic absorption in the infrared region at the following wavelengths in microns: 3.05, 3.40, 5.70, 5.77, 5.93, 6.07, 6.62, 6.82 and 7.67.

3. Antibiotic substance Compound 36,926 having the average composition by weight of 57.89% carbon, 6.78% hydrogen, 8.04% nitrogen and 27.29% oxygen (by difference) and the molecular formula $C_{26}H_{35}N_3O_7$; having an optical rotation of $[\alpha]_D^{25°} = -130°$ at a concentration of 1% in ethanol; absorption maxima in ethanol in the ultraviolet light region of the spectrum at 214 m$\mu$ with $E_{1\ cm}^{1\%}$ of 723.8; and when pelleted in KBr exhibiting characteristic absorption in the infrared region at the following wavelengths in microns: 2.95, 3.40, 5.75, 5.98, 6.23, 6.58, 6.87, 7.45, 8.25, 8.38, 8.80, 9.08, 10.15, 10.35, 11.10 and 13.30.

4. Antibiotic substance Compound 37,932 which in crystalline form has an optical rotation of $[\alpha]_D^{25°} = +5.0°$ at a concentration of 0.25% in chloroform; absorption maxima in ethanol in the ultraviolet light region of the spectrum at 226, 276, 283, 305 and 355 m$\mu$ with $E_{1\ cm}^{1\%}$ values of 304.4, 36.8, 43.49, 70.25 and 20.07, respectively; having the average composition by weight of 59.41% carbon, 6.01% hydrogen, 10.66% nitrogen and 23.92% oxygen (by difference); and when pelleted in KBr exhibiting characteristic absorption in the infrared region at the following wavelengths in microns: 2.96, 3.05, 3.38, 5.68, 5.73, 5.93, 5.98, 6.13, 6.50, 6.58, 6.88, 7.40, 7.65, 8.08, 8.45, 8.60, 9.03, 9.45, 9.70, 9.98, 10.55, 11.00, 11.25, 11.60, 12.35 and 13.25.

5. Antibiotic substance Compound 40,042 which in crystalline form has an optical rotation of $[\alpha]_D^{25°} = -1.7°$ at a concentration of 1.0% in ethanol; absorption maxima in ethanol in the ultraviolet light region of the spectrum at 230, 278, 282, 294, 303 and 355 m$\mu$ with $E_{1\ cm}^{1\%}$ values of 249.2, 69.77, 75.60, 89.10, 91.81 and 91.97, respectively; having the average composition by weight of 61.08% carbon, 6.23% hydrogen, 10.75% nitrogen and 21.94% oxygen (by difference); and when pelleted in KBr exhibiting characteristic absorption in the infrared region at the following wavelengths in microns: 2.92, 2.97, 3.37, 5.67, 5.70, 6.00, 6.58. 6.88, 7.68, 8.00, 8.47, 8.90, 9.04, 9.24, 9.70, 12.35 and 13.37.

* * * * *